(12) United States Patent
Jo et al.

(10) Patent No.: US 10,674,925 B2
(45) Date of Patent: Jun. 9, 2020

(54) ELECTRODE ASSEMBLIES FOR MEASURING BIO-SIGNALS

(71) Applicant: SAMSUNG ELECTRONICS CO., LTD., Suwon-si, Gyeonggi-Do (KR)

(72) Inventors: Hee-Jae Jo, Suwon-si (KR); Se-Hoon Lim, Suwon-si (KR); Hyungjong Ko, Seongnam-si (KR); Yongin Park, Seoul (KR); Min Gun Baek, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 593 days.

(21) Appl. No.: 15/398,734

(22) Filed: Jan. 5, 2017

(65) Prior Publication Data

US 2017/0188863 A1 Jul. 6, 2017

(30) Foreign Application Priority Data

Jan. 5, 2016 (KR) .................. 10-2016-0001004

(51) Int. Cl.
*A61B 5/0416* (2006.01)
*A61B 5/0402* (2006.01)
*A61B 5/0492* (2006.01)
*A61B 5/0478* (2006.01)
(Continued)

(52) U.S. Cl.
CPC .......... *A61B 5/0402* (2013.01); *A61B 5/0416* (2013.01); *A61B 5/0476* (2013.01); *A61B 5/0478* (2013.01); *A61B 5/0488* (2013.01); *A61B 5/0492* (2013.01)

(58) Field of Classification Search
CPC ... A61B 5/0402; A61B 5/0416; A61B 5/0478; A61B 5/0488; A61B 5/0492; A61B 50/417; A61B 5/04; A61B 5/0408; A61B 5/0476; A61B 2562/221; A61B 2562/225; A61B 2562/222; A61B 2562/227; A61B 2562/22; H01R 4/4827; H01R 4/48;
(Continued)

(56) References Cited

U.S. PATENT DOCUMENTS

| 4,671,591 | A | * | 6/1987 | Archer | ................. A61B 5/0416 439/346 |
| 5,176,543 | A | * | 1/1993 | Brooks | .................. A61N 1/048 439/859 |
| 7,950,971 | B2 | | 5/2011 | Hobet et al. | |

(Continued)

FOREIGN PATENT DOCUMENTS

JP 2008-006096 A 1/2008
JP 2013-042798 A 3/2013
(Continued)

*Primary Examiner* — Eun Hwa Kim
*Assistant Examiner* — Adam Z Minchella
(74) *Attorney, Agent, or Firm* — Volentine, Whitt & Francos, PLLC

(57) ABSTRACT

An electrode assembly for measuring bio-signals includes a body, a fastening member extending from the body and provided on one side of the body, the fastening member including a spring groove formed therein and an aperture penetrating therethrough, and a spring inserted into the spring groove. The aperture receives a fastening stud of a patch which is supplied from outside. The spring compresses the fastening stud received in the aperture such that the fastening member fixes the fastening stud thereto.

14 Claims, 5 Drawing Sheets

(51) Int. Cl.
*A61B 5/0476* (2006.01)
*A61B 5/0488* (2006.01)

(58) Field of Classification Search
CPC ...... H01R 4/4809; H01R 4/52; H01R 4/4818; H01R 2201/12; G01L 19/0084
See application file for complete search history.

(56) References Cited

U.S. PATENT DOCUMENTS

| | | | |
|---|---|---|---|
| 7,993,167 | B2 | 8/2011 | Keightley et al. |
| 8,123,576 | B2 | 2/2012 | Kim |
| 8,214,007 | B2* | 7/2012 | Baker .................. A61B 5/0006 600/372 |
| 8,251,736 | B2 | 8/2012 | McIntire et al. |
| 8,328,563 | B2 | 12/2012 | Ruiter |
| 8,406,843 | B2 | 3/2013 | Tiegs et al. |
| 8,795,004 | B2 | 8/2014 | Selvitelli et al. |
| 2007/0078324 | A1 | 4/2007 | Wijiskiwardana |
| 2010/0075527 | A1* | 3/2010 | McIntire .............. A61B 5/0416 439/357 |
| 2010/0297868 | A1* | 11/2010 | Hermannsson .... A61B 5/04085 439/345 |
| 2011/0201913 | A1* | 8/2011 | Kim ..................... A61B 5/0416 600/394 |
| 2012/0143034 | A1* | 6/2012 | Gaw .................... A61B 5/0416 600/393 |

FOREIGN PATENT DOCUMENTS

| | | |
|---|---|---|
| JP | 2013-042813 A | 3/2013 |
| JP | 2013-184024 A | 9/2013 |
| JP | 2014-226172 A | 12/2014 |
| JP | 2015-073623 A | 4/2015 |

* cited by examiner

ELECTRODE ASSEMBLIES FOR MEASURING BIO-SIGNALS

PRIORITY STATEMENT

This U.S. nonprovisional patent application claims priority under 35 U.S.C. § 119 of Korean Patent Application 10-2016-0001004 filed on Jan. 5, 2016, the entire contents of which are hereby incorporated by reference.

BACKGROUND

The present inventive concept relates to an electrode assembly attachable to a monitoring patch adhered to a human body for measuring bio-signals.

FIG. 1 is a perspective view illustrating a conventional electrode assembly. Referring to FIG. 1, in order to measure bio-signals such as electrocardiograms, electromyograms, brain waves, nervous system signals, etc., a universal patch 13 may be adhered to a human body and coupled to an electrode assembly 10 and the electrode assembly 10 may transfer bio-signals obtained from the universal patch 13 to monitoring apparatus. The electrode assembly 10 may be removably attachable to the universal patch 13. The electrode assembly 10 may include a body 15 made of a metallic material, and the body 15 may include an extrusion 15a. The extrusion 15a may provided a space in which a fastening stud 14 of the universal patch 13 is placed when the fastening stud 14 is attached to the body 15. The body 15 may be coupled to a wire 12 by a weld or the like. The electrode assembly 15 may further include a casing 11 that covers the body 15 and the wire 12 coupled to the body 15. The casing 11 may be formed of synthetic resin by injection molding. Since the fastening stud 14 is inserted into the body 15, the body 15 must have a thickness 15T greater than that 14T of the fastening stud 14.

SUMMARY

According to some examples of the inventive concept, an electrode assembly for measuring bio-signals comprises a body, a fastening member extending from the body at one side of the body, and a spring. The fastening member includes a spring groove therein and an aperture extending therethrough. The spring is seated in the spring groove. The aperture is sized and shaped to receive a fastening stud of a patch, and the spring is configured to clamp the fastening stud received in the aperture to the fastening member to fix the fastening stud to the electrode assembly.

According to some examples of the inventive concept, an electrode assembly comprises a housing, electronic components disposed in the housing and configured to detect bio-signals, a plate extending laterally from the housing and having an aperture extending vertically therethrough, and a clip integrated with the plate and having arms disposed at opposite sides of the aperture.

According to some examples of the inventive concept, apparatus for measuring bio-signals comprises a combination of an electrode assembly and a patch. The electrode assembly comprises a body, a fastening member and a spring. The fastening member extends from the body at one side of the body, and the fastening member has a spring groove therein and an aperture therethrough. The spring is seated in the spring groove. The patch comprises a membrane and a fastening stud fixed to and extending upright on the membrane. The aperture receives the fastening stud of the patch, and the spring clamps the fastening stud, received in the aperture, to the fastening member thereby fixing the fastening stud to the electrode assembly. A thickness of the fastening member is less than a thickness of the fastening stud as each measured in a vertical direction from the membrane of the patch.

BRIEF DESCRIPTION OF THE DRAWINGS

The accompanying drawings are included to provide a further understanding of the inventive concept, and are incorporated in and constitute a part of this specification. The drawings illustrate examples of the inventive concept and, together with the description, serve to explain principles of the inventive concept. In the drawings.

DETAILED DESCRIPTION

Figure 3:
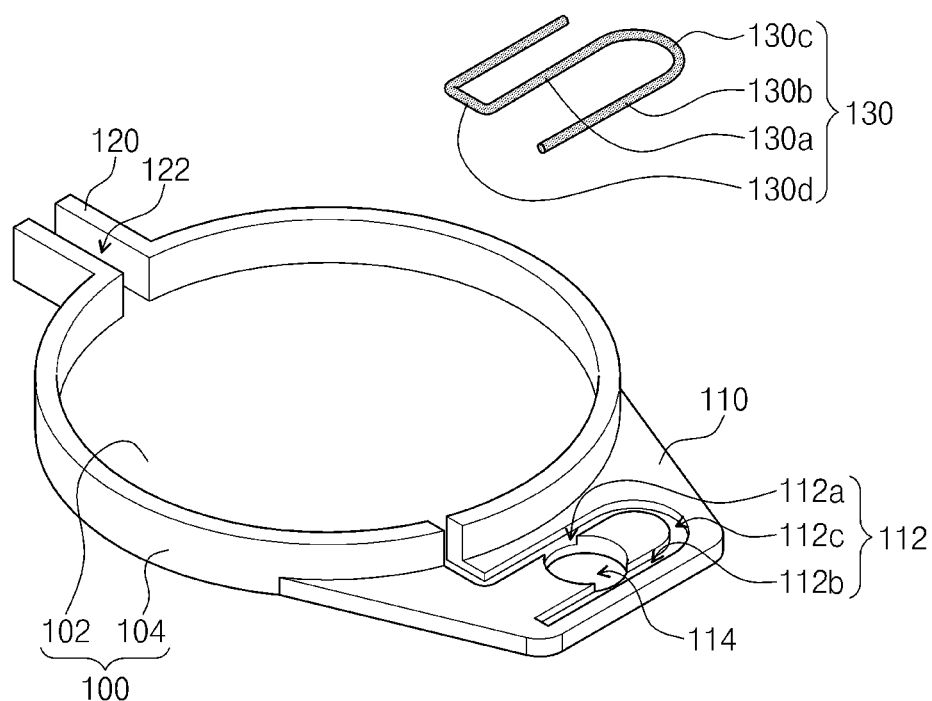
FIG. 3 is a perspective view of a portion of the electrode assembly of FIG. 2.
Figure 4:
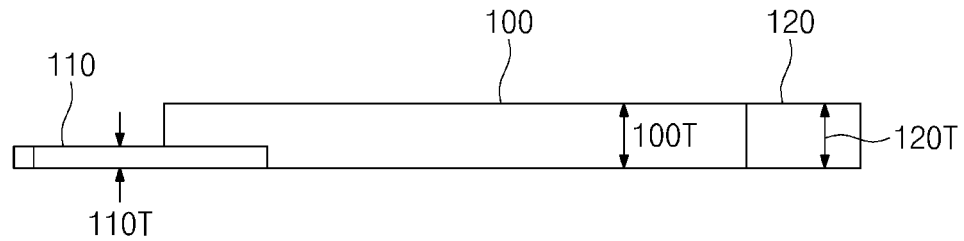
FIG. 4 is a side view of the electrode assembly of FIG. 2.

First, an example of an electrode assembly according to the inventive concept will be described hereinafter in conjunction with FIGS. 2 through 4.

The electrode assembly 200 may include a body 100, a fastening member 110 that extends from the body 100 and which is to be coupled to a patch 160, and a connection member 120 that extends from the body 100 and is adapted to guide an external wire 124 into the body 100.

The body 100 may include a base 102 and a sidewall 104 projecting upward from the base 102 and extending along a circumference of the base 102. The body 100 may have a cavity therein (surrounded and delimited by the sidewall 104), and the cavity may receive an electronic components 106 (e.g., a printed circuit board, etc.) for measuring bio-signals.

The fastening member 110 may have a grooved upper surface that defines a spring groove 112, and a spring 130 may be received in the spring groove 112 so as to be seated in the upper surface of the fastening member 110. As shown in FIG. 3, the spring groove 112 may have a first straight section 112a adjacent to the sidewall 104 of the body 100, a second straight section 112b facing the first straight section 112a, and a curved section 112c connecting the first and second straight sections 112a and 112b to each other. The first straight section 112a, the curved section 112c, and the second straight section 112b may be connected with one another to collectively have a U-shape. An extension of the groove 112 may lead from the first straight section 112a through the sidewall 104 of the body 100 and thus be open to the interior of the body 100. The spring 130 may have a first straight portion 130a, a second straight portion 130b facing the first straight portion 130a, and a curved portion 130c connecting the first and second straight portions 130a and 130b to each other. The first straight portion 130a, the curved portion 130c, and the second straight portion 130b may be connected with one another to collectively have a U-shape. In some examples, the spring 130 may further include an extension 130d extending form an end of the first straight portion 130a. In other examples, the spring 130 has no such extension 130d, e.g., may only have first straight portion 130a, the curved portion 130c, and the second straight portion 130b so as to be collectively U-shaped.

The first straight portion 130a, the curved portion 130c, and the second straight portion 130b of the spring 130 may be respectively received in the first straight section 112a, the curved section 112c, and the second straight section 112b of the spring groove 112. The extension of the spring groove 112 may receive and guide the extension 130d of the spring 130 into the body 100. When the electronic components 106 (e.g, circuitry supported by a printed circuit board) for measuring bio-signals is received in the case that the body, the extension 130d of the spring 130 may be electrically connected to the electronic components 106. In examples in which the spring 130 does not have the extension 130d, the first straight portion 130a may be electrically connected to the electronic components 106 through other connection means (e.g., a metal wire discrete from the spring 130).

The fastening member 110 may have an aperture 114 therethrough. The aperture 114 may be provided between the first straight section 112a and the second straight section 112b of the spring groove 112. The aperture 114 may open into the first and second straight sections 112a and 112b of the spring groove 112.

The connection member 120 may have a wire groove 122 therein. The wire groove 122 may penetrate the sidewall 104 of the body 100 so as to be open to the interior (cavity) of the body 100. The wire groove 122 may guide the wire 124 inserted thereinto from the outside, and thus the wire 124 may extend through the sidewall 104 of the body 100 into the body 100. When the electronic components 106 (e.g, a printed circuit board, etc.) for measuring bio-signals is receive in (the cavity of) the body 100, the electronic components 106 may be electrically connected to an end of the wire 124 received in the body 100. Although not shown in the figures, the other end of the wire 124 may be coupled to another electrode assembly so as to connect the electrode assemblies for measuring bio-signals.

In some examples, the fastening member 110 and the connection member 120 are disposed across from each other with the body 100 interposed therebetween, but the inventive concept is not limited thereto. As shown in FIG. 4, the fastening member 110 may have a thickness 110T less than a thickness 100T of the body 100, and the connection member 120 may have a thickness 120T substantially the same as or less than a thickness 100T of the body 100.

The electrode assembly 200 may include a first casing 140 that covers the body 100 and the connection member 120 and a second casing 150 that covers the fastening member 110. The first casing 140 may be fixed relative to the sidewall 104 and form a cover that closes or seals the cavity of the body 100 and the wire groove 122 of the connection member 120. Thus, the first casing 140 and the body 100 may together form a housing containing the electronic components 105. The second casing 150 may close or seal the spring groove 112 of the fastening member 110. The second casing 150 may thus be a cover that retains the spring 130 in the spring groove 112 of the fastening member 100. Also, the fastening member 110 is within the thickness of the housing and in some examples, has a bottom surface that is coplanar with the bottom surface of the base 102.

The second casing 150 may have a casing hole 152 therethrough. The casing hole 152 may overlap the aperture 114 of the fastening member 110, in a plan view. In some examples, the second casing 150 has no such casing hole 152. In some examples, as shown in FIG. 2, the first casing 140 and the second casing 150 may be independent components discrete from each other. Alternatively, the first casing 140 and the second casing 150 may be integral with one another or more specifically, may be unitary, i.e., may constitute a single component.

The body 100, the fastening member 110, the connection member 120, the first casing 140, and the second casing 150 may be formed of an insulative material such as plastic by injection molding. The spring 130 and the wire 124 may be formed of a conductive material such as metal. Although not shown in figures, at least a portion of the wire 124 which is exposed outside the electrode assembly 200 may be coated with an insulative material such as a synthetic resin.

Figure 1:
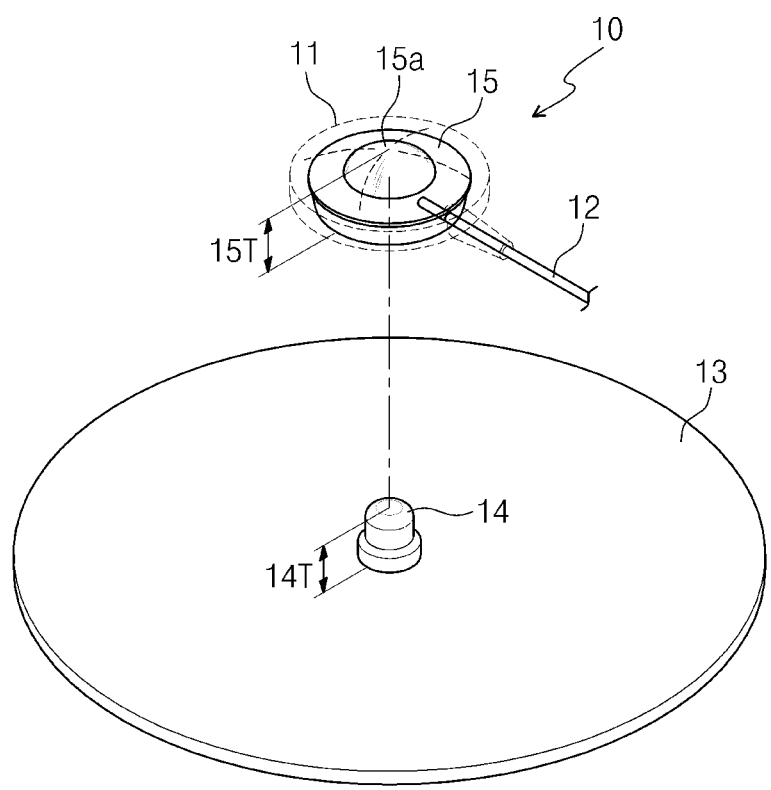
FIG. 1 is a perspective view of a conventional electrode assembly.
Figure 2:
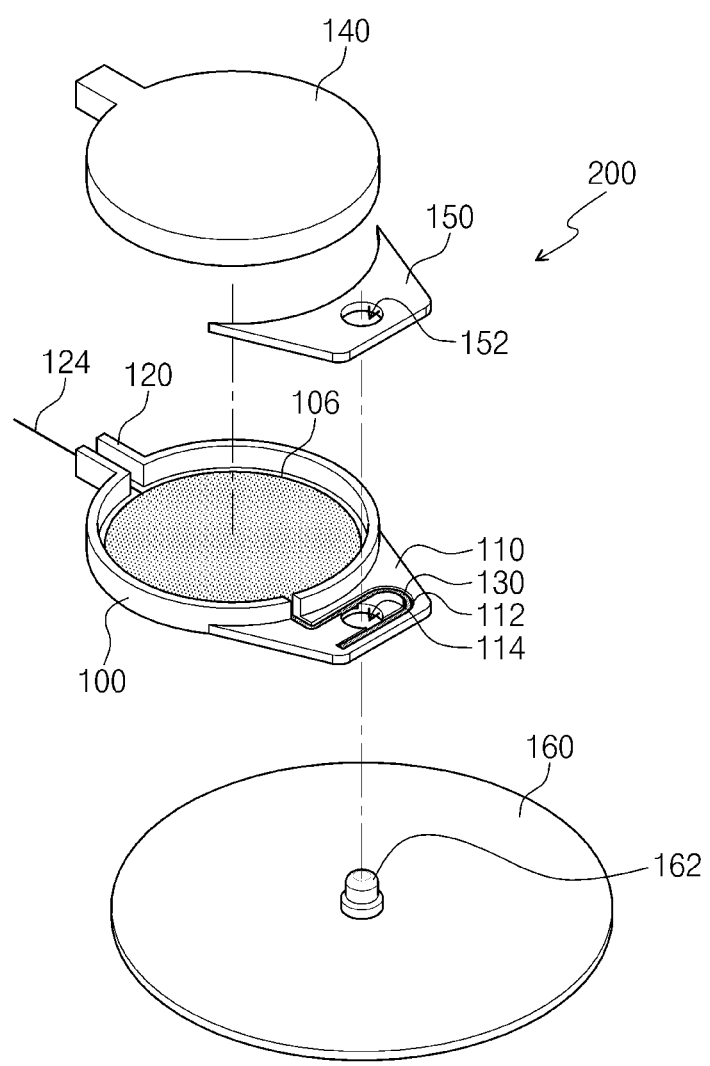
FIG. 2 is an exploded perspective view of an example of an electrode assembly according to the inventive concept.
Figure 5:
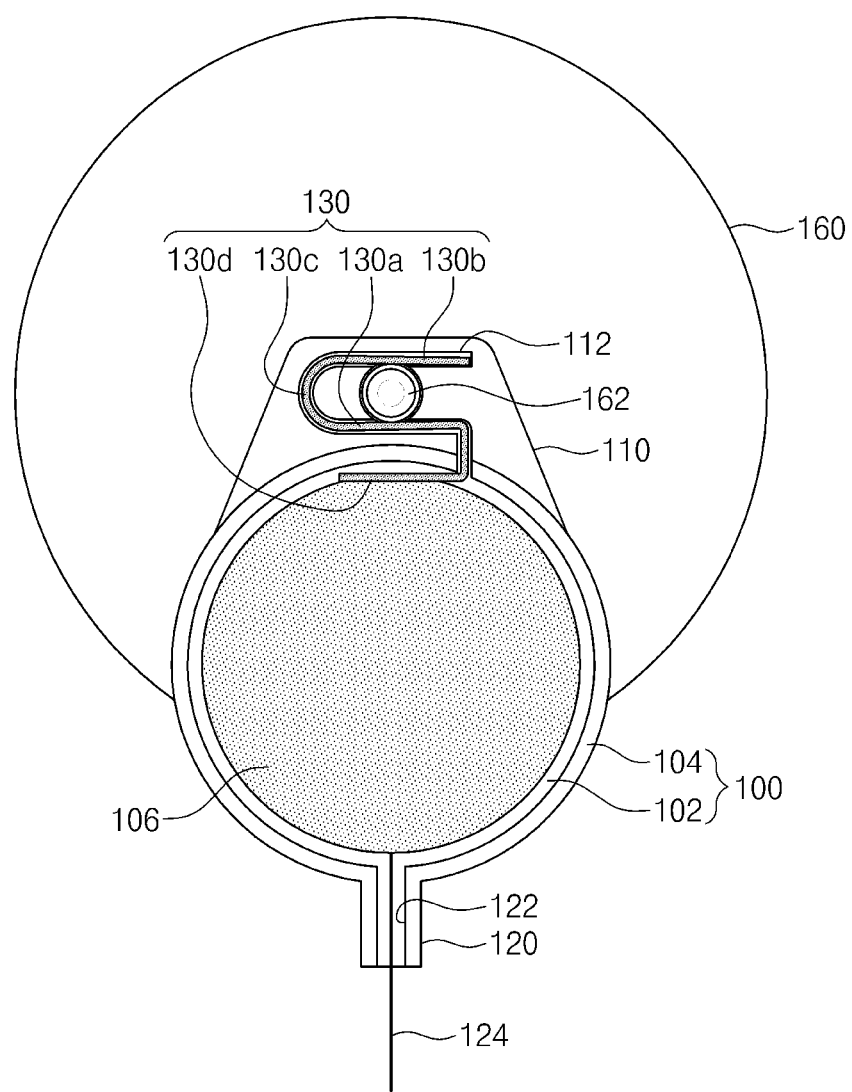
FIG. 5 is a plan view of an electrode assembly combined with a universal patch according to the inventive concept.
Figure 6:
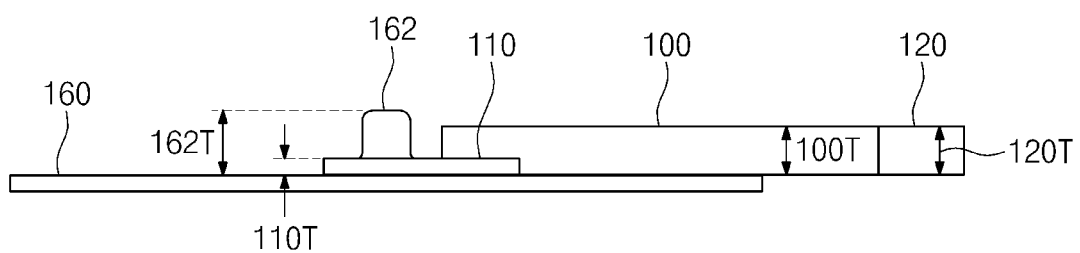
FIG. 6 is a side view of the combination shown in FIG. 5.

Referring to FIGS. 2, 5 and 6, the fastening member 110 may attach the electrode assembly 200 to the patch 160. The patch 160 may be adhered to a human body such that bio-signals such as electrocardiograms, electromyograms, brain waves, nervous system signals, etc. can be measured. The patch 160 may include a patch membrane and a fastening stud 162 fixed to and extending upright on the membrane, and the fastening stud 162 may pass through the aperture 114, i.e., may be inserted into the fastening member 110. The aperture 114 may have a size and shape that enables the aperture 114 to receive the fastening stud 162. When the fastening stud 162 extends through the aperture 114, i.e., extends into the fastening member 110, the fastening stud 162 is interposed between the first straight portion 130a and the second straight portion 130b of the spring 130. The diameter of the fastening stud 162 is slightly greater than the distance between the first and second straight portions 130a and 130b of the spring 130. Thus, the fastening stud 162 may compressed or clamped by and between the first and second straight portions 130a and 130b of the spring 130, and thereby fixed to the fastening member 110. That is, in some examples the spring 130 is a hairpin clip that clamps the fastening stud 162 to the fastening member 110 and thereby fixes the patch 160 to the electrode assembly 200. In such examples the first and second portions 130a and 130b are arms of the hairpin clip, respectively.

Accordingly, the electrode assembly 200 may be (removably) attached to the patch 160.

When (the membrane of) the patch 160 is adhered to a human body, bio-signals from the body may be transferred to the electronic components 106 (e.g., a printed circuit board, etc.) in the body of the electrode assembly 200, through the spring 130 and the fastening stud 162 formed of metal.

Also, when the fastening stud 162 is attached to the fastening member 110 in the manner described above, a head of the fastening stud 162 may pass through the casing hole 152 of the second casing 150. In this case, the fastening stud 162 may be detached from the fastening member 110 by pushing down on the head of the fastening stud 162 projecting from the second casing 150. Specifically, when the head of the fastening stud 162 is pushed down, the downward force on the stud 162 may act to spread the first and second straight portions 130a and 130b of the spring 130 apart such that the fastening stud 162 is released from the fastening member 110 and can be withdrawn through the aperture 114.

As shown in FIG. 6, the thickness 110T of the fastening member 110 may be less than a thickness 162T of the fastening stud 162. Thus, the head of the fastening stud 162 may project from the fastening member 110 in a state in which the fastening stud 162 is attached to the fastening member 110.

In some examples as described above, the electrode assembly 200 includes the fastening member 110 extending from the body 100 and provided on one side of the body 100. The spring 130 is provided in the fastening member 110 to fix the fastening stud 162 of the patch 160 to the electrode assembly 200. When the patch 160 is adhered to a human body, bio-signals from the human body can be transferred to the electronic components 106 (e.g., a printed circuit board, etc.) provided in the cavity of the body 100 through the spring 130 and the fastening stud 162. In other words, the spring 130 may be used as means for transferring bio-signals and for engaging the fastening stud 162. In these examples, therefore, the electrode assembly 200 has a minimal number of parts and is easy to fabricate.

In addition, the thickness 110T of the fastening member 110 may be less than the thickness 162T of the fastening stud 162, which allows the thickness of the electrode assembly 200 to be kept to a minimum. Accordingly, an electrode assembly according to the inventive concept may offer an advantage of providing a relatively comfortable fit when the electrode assembly 200 is attached to a patch is adhered to a human body.

Although the inventive concept has been described in connection with various examples thereof, it is not limited to such examples. Rather, it will be apparent to those skilled in the art that various substitutions, modifications and changes may be imparted to the disclosed examples without departing from the scope and spirit of the inventive concept.

What is claimed is:

1. An electrode assembly for measuring bio-signals, comprising:
   a body;
   a fastening member outside the body and extending from a sidewall of the body at one side of the body, the fastening member including a spring groove therein and an aperture extending through the fastening member; and
   a spring seated in the spring groove of the fastening member,
   wherein the aperture is sized and shaped to receive a fastening stud of a patch, and the spring is configured to clamp the fastening stud received in the aperture to the fastening member to thereby fix the fastening stud to the electrode assembly,
   the body includes a base and the sidewall extending upright on the base and delimiting a cavity in the body,
   the spring groove has a first straight section adjacent to the sidewall of the body, a second straight section facing the first straight section, and a curved section connecting the first straight section to the second straight section, and
   the spring groove has an extension section leading from the first straight section and open to the cavity through the sidewall of the body.

2. The electrode assembly of claim 1, wherein the first straight section, the second straight section, and the curved section connect to one another such that said sections collectively are U-shaped.

3. The electrode assembly of claim 1, wherein the aperture is located between the first straight section and the second straight section of the spring groove.

4. The electrode assembly of claim 3, wherein the aperture opens into the first straight section and the second straight section of the spring groove.

5. The electrode assembly of claim 1, wherein the spring has a first straight portion received in the first straight section of the spring groove, a second straight portion received in the second straight section of the spring groove, and a curved portion received in the curved section of the spring groove, and
   the first straight portion, the second straight portion, and the curved portion of the spring collectively are U-shaped.

6. The electrode assembly of claim 1, wherein the spring further comprises an extension, and
   the extension of the spring extends through the sidewall of the body as received in and guided by the extension section of the spring groove.

7. The electrode assembly of claim 5, wherein the aperture is located between the first straight section and the second straight section of the spring groove,
   whereby the first and second straight portions of the spring compress the fastening stud received in the aperture to fix the fastening stud to the fastening member.

8. The electrode assembly of claim 1, wherein at least one of the body and the fastening member is formed of an insulative material.

9. The electrode assembly of claim 8, wherein the spring is formed of a conductive material.

10. The electrode assembly of claim 9, wherein
    the electrode assembly further comprising electronic components configured to measure bio-signals and disposed in the cavity of the body, and electrically connected to the spring.

11. The electrode assembly of claim 10, further comprising:
    a first casing that covers the body and closes off the cavity of the body from an environment outside the electrode assembly; and
    a second casing that covers the fastening member and the spring received in the spring groove.

12. An electrode assembly for measuring bio-signals, comprising:
    a body;
    a fastening member outside the body and extending from a sidewall of the body at one side of the body, the fastening member including a spring groove therein and an aperture extending through the fastening member; and
    a spring seated in the spring groove of the fastening member,
    wherein the aperture is sized and shaped to receive a fastening stud of a patch, and the spring is configured to clamp the fastening stud received in the aperture to the fastening member to thereby fix the fastening stud to the electrode assembly,
    the body includes a base and the sidewall extending upright on the base and delimiting a cavity in the body, and
    the electrode assembly further comprising a connection member that extends from the body on a side of the body opposite that from which the fastening member extends from the body, the connection member having a wire groove therein that is open to the cavity through the sidewall of the body.

13. The electrode assembly of claim 12, further comprising:
    a wire received in the wire groove; and
    electronic components configured to measure bio-signals provided in the cavity of the body,
    wherein the wire extends into the cavity and is electrically connected to the electronic components.

14. The electrode assembly of claim 12, including the patch, the patch comprising a membrane and the fastening stud fixed to and extending upright on the membrane.

* * * * *